United States Patent
McNamara et al.

(10) Patent No.: US 8,778,321 B2
(45) Date of Patent: Jul. 15, 2014

(54) MODIFICATION OF CELLULOSIC SUBSTRATES TO CONTROL BODY ODOR

(75) Inventors: John J. McNamara, El Sobrante, CA (US); William Ware, Jr., Hanover, NH (US); Wenxin Yu, San Ramon, CA (US)

(73) Assignee: Nanotex LLC, Bloomfield Hills, MI (US)

( * ) Notice: Subject to any disclaimer, the term of this patent is extended or adjusted under 35 U.S.C. 154(b) by 645 days.

(21) Appl. No.: 12/286,415

(22) Filed: Sep. 30, 2008

(65) Prior Publication Data

US 2009/0092572 A1 Apr. 9, 2009

Related U.S. Application Data

(60) Provisional application No. 60/997,261, filed on Oct. 1, 2007.

(51) Int. Cl.
| | | |
|---|---|---|
| *D06M 15/267* | (2006.01) | |
| *D06M 15/285* | (2006.01) | |
| *D06M 15/29* | (2006.01) | |
| *D06M 15/347* | (2006.01) | |

(52) U.S. Cl.
USPC ....... 424/76.1; 427/389.9; 427/332; 427/396; 442/123; 524/560; 524/850; 526/303.1; 526/306; 526/304

(58) Field of Classification Search
USPC .............. 427/389.9, 332, 76.1; 442/123, 396; 524/560, 850; 526/303.1, 306, 403
See application file for complete search history.

(56) References Cited

U.S. PATENT DOCUMENTS

| | | | |
|---|---|---|---|
| 2,982,751 A | 5/1961 | Anthes | |
| 3,021,232 A | 2/1962 | Pretka | |
| 3,376,245 A | 4/1968 | Sample, Jr. et al. | |
| 3,383,162 A | 5/1968 | Whitfield et al. | |
| 3,622,528 A | 11/1971 | Longoria, III | |
| 3,807,946 A | 4/1974 | Harper, Jr. et al. | |
| 3,885,069 A | 5/1975 | Roberts et al. | |
| 4,011,613 A | 3/1977 | Bertoniere et al. | |
| 4,244,059 A | 1/1981 | Pflaumer | |
| 4,588,413 A | 5/1986 | Keil et al. | |
| 4,778,813 A | 10/1988 | Fenyes et al. | |
| 4,806,126 A | 2/1989 | Sternberger et al. | |
| 4,909,986 A * | 3/1990 | Kobayashi et al. | 422/4 |
| 5,139,530 A | 8/1992 | Blanchard et al. | |
| 5,242,463 A | 9/1993 | Blanchard et al. | |
| 5,298,584 A | 3/1994 | Blanchard et al. | |
| 5,300,287 A | 4/1994 | Park | |
| 5,512,064 A | 4/1996 | von der Eltz et al. | |
| 6,001,342 A | 12/1999 | Forestier et al. | |
| 6,034,129 A | 3/2000 | Mandeville, III et al. | |
| 6,077,794 A | 6/2000 | Tabata et al. | |
| 6,187,856 B1 | 2/2001 | Incorvia et al. | |
| 6,679,924 B2 | 1/2004 | Ware et al. | |
| 6,730,740 B1 * | 5/2004 | Mestach et al. | 525/192 |
| 7,141,077 B2 | 11/2006 | Detering et al. | |
| 2002/0103278 A1 * | 8/2002 | Krajnik et al. | 524/192 |
| 2004/0166753 A1 * | 8/2004 | Millward et al. | 442/123 |
| 2006/0162090 A1 | 7/2006 | Offord | |
| 2008/0163437 A1 | 7/2008 | Fang et al. | |

FOREIGN PATENT DOCUMENTS

| | | |
|---|---|---|
| CA | 1178631 | 11/1984 |
| EP | 0889158 | 1/1999 |
| GB | 1549012 | 8/1979 |
| WO | 8201993 | 6/1982 |
| WO | 9734040 | 9/1997 |
| WO | 02095122 | 11/2002 |
| WO | 02101140 | 12/2002 |
| WO | 2004044305 | 5/2004 |

OTHER PUBLICATIONS

WIPO/PCT, Written Opinion of International Searching Authority with International Search Report, mailed Nov. 26, 2008, International Pat. Appln. PCT/US2008/011288 (corresponding to the present U.S. Appl. No. 12/286,415).

International Preliminary Report on Patentability mailed on Apr. 7, 2010 in PCT/US2008/011288.

* cited by examiner

*Primary Examiner* — Satya Sastri

(74) *Attorney, Agent, or Firm* — Brooks Kushman P.C.

(57) ABSTRACT

A finish for cellulosic fibrous substrates containing tertiary amine-containing polymers for providing durable control of body odors and the cellulosic materials treated with the finish, which materials exhibit little or no discoloration and little or no degradation of physical strength as a result of the treatment.

21 Claims, No Drawings

MODIFICATION OF CELLULOSIC SUBSTRATES TO CONTROL BODY ODOR

This application claims the benefit of U.S. Provisional application Ser. No. 60/997,261, filed Oct. 1, 2007, the entire disclosure of which is incorporated herein by reference.

TECHNICAL FIELD

The present application relates to cellulosic materials treated with amine-containing polymers, which materials exhibit no discoloration and no degradation of physical strength as a result of the treatment.

BACKGROUND OF THE INVENTION

Cellulosic fiber and fabrics could be enhanced certain desired performance through finish. Various amine-containing finishes have been developed to enhance different performances on fabrics.

Durability is a basic requirement for commercial textile chemical finishes. While U.S. Pat. No. 4,244,059, issued to Pflaumer, teaches application of water-soluble polyamines on a panty type garment, there is no laundry durability expected from this finish because water-soluble polyamines dissolve in water and wash away after laundry.

U.S. Pub. No. 2004/0166753, Millward and Ware, teaches finishes for cellulosic fibrous substrates comprising polymers with amine groups containing primary, secondary and/or tertiary amines, crosslinkers and a volatile solvent. However, color change is a challenge for amine-containing finish on celluosic materials. Amino groups can cause yellowing or discoloration upon exposure to high heat during curing.

U.S. Pub. No. 2006/0162090 A1, Offord, describes durable finish comprising hydroxyl-containing amines combined with the preferred crosslinker dimethyloldihydroxyethyl-eneurea (DMDHEU) on fibrous substrate to reduce body odor. U.S. Pat. No. 5,139,530, issued to Blanchard et al., teaches production of anionically dyeable cellulosic materials by treatment of hydroxyalkyamine and DMDHEU prior to dyeing. However, it is well known in the textile industry that treatment of cellulosic fabrics with the resin system DMDHEU dramatically impairs cotton physical properties, e.g., tensile strength, tear strength, etc. The mobility of the cellulosic molecule is frozen during thermosetting in the presence of DMDHEU. This leads to brittleness of the fabrics treated with DMDHEU.

Thus, it is desirable to provide a method to attach tertiary amine on the cellulosic fabrics without damaging the physical properties, while at the same time preventing discoloration of the treated fabric.

SUMMARY OF THE INVENTION

The present invention is directed to durable finishes for cellulose-containing fibers and fibrous substrates. The durable finish comprises (i) a tertiary amine-containing polymer, (ii) a suitable crosslinker, and (iii) a volatile solvent. More particularly, the invention is directed to a durable finish for cellulosic fibrous substrates comprising a tertiary amine-containing polymer of formula (I):

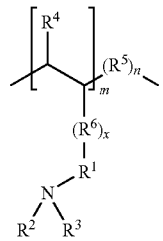

wherein each of $R^1$, $R^2$ and $R^3$ is independently an alkyl group, a hydroxyalkyl group or a tertiary amine-containing alkyl group; $R^4$ is hydrogen or an alkyl group; $R^5$ is a hydroxyl-reactive functional group; $R^6$ is an ester group, an ether group, an amide group or a tertiary amine-containing alkyl group; each of m and n is independently a positive integer of about 10 to about 1,000,000; and x is zero or one. The tertiary amine-containing polymers are polymerized from appropriate monomers. Polymer (I) can be a copolymer of any constitution, such as, for example, a block copolymer or a random copolymer.

The finishes of this invention impart durable control of certain odors, such as body odor, to the cellulosic fabric surface. At the same time, the fibrous substrates treated with the finish exhibit substantially improved physical strength compared to prior art treatments, and the color change of dyed fabrics and yellowing of white fabrics are also eliminated.

This invention is further directed to the cellulosic fibers; yarns; woven, knitted or nonwoven fabrics and textiles; and finished goods (all of which are encompassed herein under the terms "fibrous substrates" and "fabrics") treated with the tertiary amine-containing polymer finish of the invention. The cellulosic fabrics treated with the durable finish of the invention take on properties that are not found in the native fabric, including the ability to eliminate or greatly diminish the most offensive component of malodorous body odor, while surprisingly reducing the yellowing of the substrates experienced with certain prior art amine treatments and at the same time preserving the physical strength of the native fabric, contrary to other prior art amine treatments.

DESCRIPTION OF THE INVENTION

As used herein and in the appended claims, "a" and "an" mean one or more, unless otherwise indicated.

The terms "durable" and "durability", as used herein and in the appended claims, describe a finished fibrous substrate in which the desired properties imparted to the substrate by the finish are observed after multiple launderings or dry cleanings. In one aspect, the finish of the invention is durable for at least 10 home launderings. In one aspect, the finish of the invention is durable for at least 25 home launderings. In one aspect, the finish of the invention is durable for at least 40 home launderings. In one aspect, the finish of the invention is durable for at least 50 home launderings.

The "cellulose-containing" or "cellulosic" fibrous substrates to be treated according to the present invention include any cellulosic fiber and any blend of fibers that contain a cellulosic, whether as a majority or a minority component. Cellulosic-based substrates include paper, cotton, rayon and other regenerated cellulosics and cellulose-containing materials, linen, jute, ramie, industrial hemp, and the like. In one aspect of the invention, the cellulose-containing fabric or fibrous substrate is cotton.

The finish of the invention comprises a tertiary amine-containing polymer of formula (I):

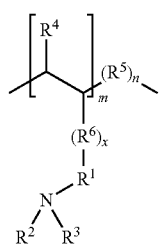

wherein each of $R^1$, $R^2$ and $R^3$ is independently an alkyl group, a hydroxyalkyl group or a tertiary amine-containing alkyl group; $R^4$ is hydrogen or an alkyl group; $R^5$ is a hydroxyl-reactive functional group; $R^6$ is an ester group, an ether group, an amide group or a tertiary amine-containing alkyl group; each of m and n is independently a positive integer of about 10 to about 1,000,000; and x is zero or one. Polymer (I) can be a copolymer of any constitution, such as, for example, a block copolymer or a random copolymer.

The tertiary amine-containing polymers are polymerized by free radical polymerization, ionic polymerization or condensation polymerization. The ratio of m to n is generally from about 1:100 to about 100:1. In one aspect, the ratio is from about 1:50 to about 50:1. In another aspect, the ratio is from about 1:10 to about 10:1.

In one embodiment, the tertiary amine-containing polymer is attached onto the cellulosic fabrics through a reactive group. In one aspect, the reactive group is N-(hydroxymethyl) acrylamide.

Physical strength, e.g. tear strength, of the fibrous substrate treated with the tertiary amine-containing polymer (I) is improved dramatically due to the absence of a resin system that includes DMDHEU and catalyst.

"Alkyl group" as used herein and in the appended claims refers to a lower alkyl group, straight-chain or branched, having from one to eight carbon atoms. In one aspect, the alkyl group has from one to six carbon atoms.

The "hydroxyl-reactive functional group" contains a terminal hydroxyl that is capable of forming bonds with cellulosic fibrous substrates, resulting in attachment of the polymer to the fibrous substrate. Hydroxyl-reactive functional groups include, but are not limited to, epoxides, halohydrins, oxiranes, carbonyl diimidazole, N,N'-dissuccinidyl carbonate, and N-hydroxylsuccinimethylol ureas. In one aspect of the invention, the hydroxyl-reactive functional group is N-(hydroxymethyl)acrylamide.

The "tertiary amine-containing polymer" encompasses oligomers as well as polymers. The tertiary amine-containing polymer may be a homopolymer, a copolymer, or a terpolymer. A copolymer may contain one or more polyacrylates with tertiary amine groups. Exemplary tertiary amine-containing polymers include, but are not limited to, poly[N,N-(dimethylaminoethyl)aminoethyl methacrylate], poly[N,N-(diethylamino)ethyl methacrylate] and poly[N,N-(diethylamino)methyl methacrylate]. In one aspect, the tertiary amine-containing polymer is poly[N,N-(dimethylaminoethyl)aminoethyl methacrylate].

The substituent $R^6$, when present, is, in one aspect of this invention, an ester. In another aspect of the invention $R^6$, when present, is an ether group.

A catalyst may optionally be included in the finish of the invention to improve reaction efficiency.

If a hydroxyl-reactive functional group is not present, the tertiary amine-containing polymer may form a network on the surface of the fibrous substrate through the tertiary amine groups. Anionic polymers may be added to crosslink the tertiary amine-containing polymer on the substrate.

The finish solution of the invention that is applied to the fibrous substrate comprises a tertiary amine-containing polymer, a suitable crosslinker, and a volatile solvent. The solvent may be chosen from any solvent that dissolves or emulsifies the polymer and/or the crosslinker but does not react adversely with either the polymer, the crosslinker or the fibrous substrate. In one aspect of the invention, the solvent is water. In this aspect, it is desirable that the polymer and/or the crosslinker will dissolve or be emulsified in water.

The "crosslinker" as used herein may be present in the tertiary amine-containing polymer chain, or it may be a separate molecule that contains two or more functional groups that form bonds with the polymer. The pad solution preferably contains tertiary amine-containing polymer at between about 0.01% and about 75% by weight, more preferably between about 0.05% and about 50% by weight. The pad solution preferably contains a crosslinker at between about 0.001% and about 40% by weight, more preferably between about 0.01% and about 30% by weight.

The finish solution may also include other additives. For example, the finish solution may also contain a wetting agent, such as WetAid NRW (BF Goodrich Corp.), to aid the equal spread of the finish over the fibers. Additional additives can be added to the solution as needed and as known by those generally skilled in the art.

The present invention relates, in part, to a method for attaching tertiary amine-containing polymers to a fibrous substrate comprising the steps of: a) obtaining one or more tertiary amine-containing monomers, from those known in the art or by synthesis; b) copolymerizing the tertiary amine-containing monomer(s) with one or more monomers comprising a hydroxyl-reactive functional group to give a tertiary amine-containing polymer; c) applying the polymer, together with an appropriate crosslinker, to a fibrous substrate; and d) curing the substrate. The substrate can be of natural fabrics or a blend of natural and synthetic fabrics.

The finish of the invention can be applied to the cellulosic fibrous substrate by exposing the substrate to the finish solution by methods known in the art, such as dip-pad-cure, spray, fluid-flow or print. After the finish has been applied to the fibrous substrate, the substrate is dried and the finish is cured and bonded on the substrate by heating.

The finish solution may be applied to the fibrous substrate at any temperature above the freezing point and below the boiling point of the solvent. In one embodiment, the application temperature is preferably between 5 and 90° C., more preferably between 10 and 50° C., and most preferably at room temperature. The treated fabric should be cured at a temperature high enough to induce the crosslinking reaction in a short time, preferably less than five minutes, more preferably a minute or less. In one present embodiment, the curing temperature is preferably between 80 and 200° C., more preferably between 100 and 180° C.

One advantage of the finish of the present invention is that a fibrous substrate finished as described above will absorb malodor from the human body, while maintaining breathability, soft hand and hydrophilicity.

Another advantage of the present invention is that color changes and the loss of physical strength (such as tensile strength and tear strength) and other physical characteristics following treatment of cellulosic fabrics with the tertiary amine-containing acrylic polymer finish are very limited or are eliminated.

The attachment of amine groups to any substrate, not just textiles, is considered to provide a "performance enhancement" to the substrate, since amine groups serve multiple functions in addition to those discussed above. For example, amine groups serve as reactive sites for additional chemical reactions to modify the properties of the substrate, such as the attachment of other chemical moieties such as enzymes, dyes, etc.

EXAMPLES

The following information is provided to give those of ordinary skill in the art with a complete disclosure and description of how to make and use the preferred embodiments of the invention, and is not intended to limit the scope of what the inventor(s) regard(s) as his or her/their invention. Modifications of the above-described modes for carrying out the invention that are obvious to persons of skill in the art are intended to be within the scope of the claims. All publications, patents, and patent applications cited in this specification are incorporated herein by reference as if each such publication, patent or patent application were specifically and individually indicated to be incorporated herein by reference.

Example 1

Synthesis of Acrylic Tertiary Amine Monomer

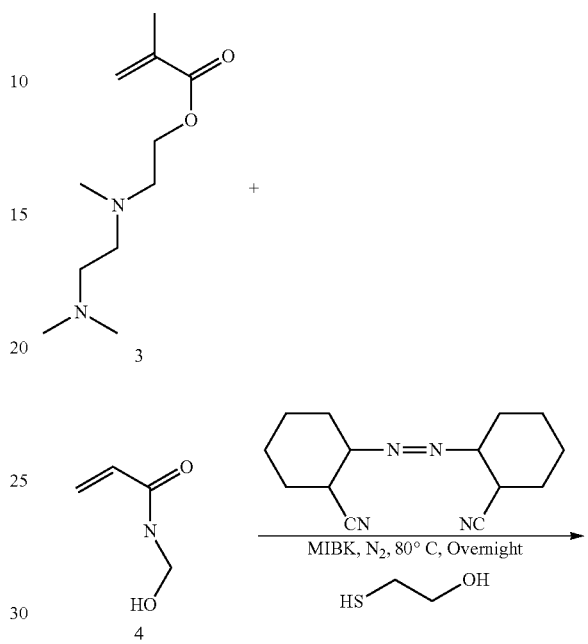

A 500 mL three-neck flask was charged with 38 g of 2-{[2-(dimethylamino)-ethyl]methylamino}ethanol (1), 101 g of triethyl amine and 100 g of methylene chloride. The solution was stirred at 350 rpm under nitrogen. 26 g of methacryloyl chloride (2) in 100 g of methylene chloride was added in the flask slowly. The suspension was refluxed for an additional 4 hours. The suspension was filtered and the solvent was removed by distillation at 40° C. Triethyl amine was removed by vacuum distillation at 50° C. Yield of product (3): 39 g, 74% (w/w).

Example 2

Polymerization

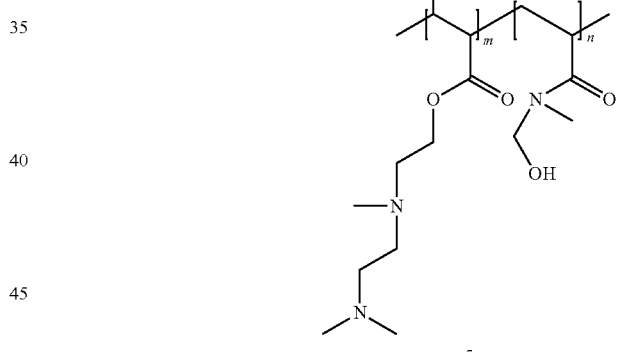

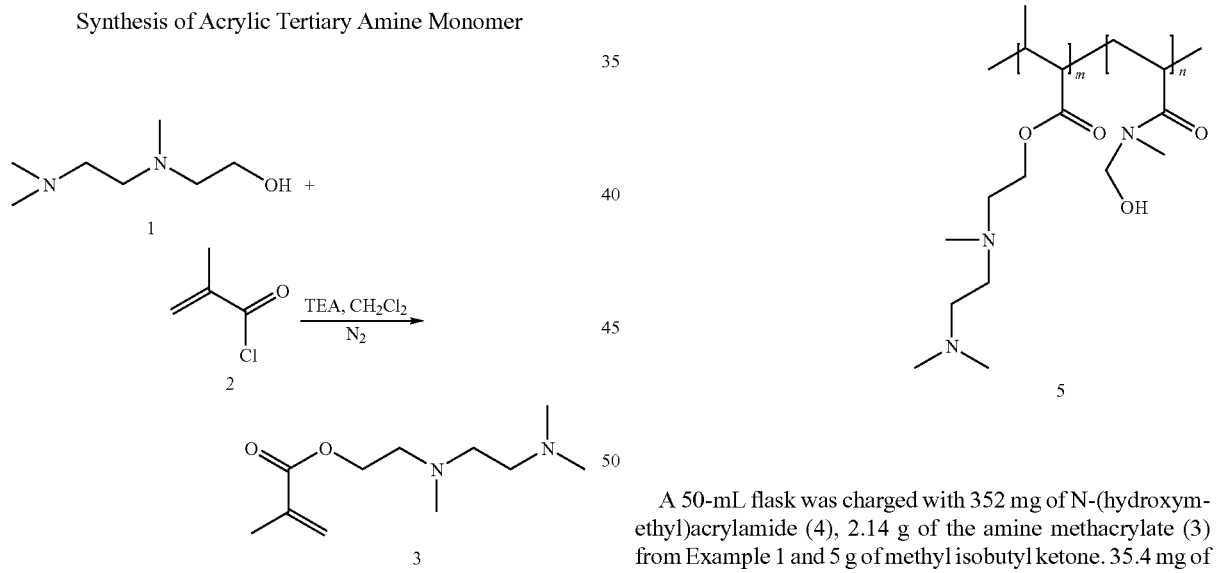

A 50-mL flask was charged with 352 mg of N-(hydroxymethyl)acrylamide (4), 2.14 g of the amine methacrylate (3) from Example 1 and 5 g of methyl isobutyl ketone. 35.4 mg of the initiator 1,1'-azobis(cyclohexanecarbonitrile) (Vazo® 88, Dupont) and 9.93 µl of 2-mercaptoethanol were then charged in the flask. The solution was stirred overnight at 80° C. under nitrogen. The solvent was removed under vacuum and a light yellow solid acrylic polymer (5) was obtained (where the ratio of m to n is about 6:1).

Example 3

Other acrylic polymers with tertiary amine were also polymerized according to the same procedure as in Example 2. The starting monomers are shown in Table A below:

TABLE A

| | Starting monomers |
|---|---|
| i | 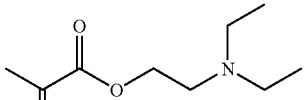 and 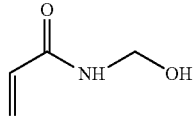 |
| ii | 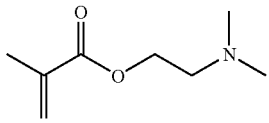 and 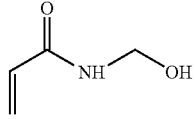 |
| iii | 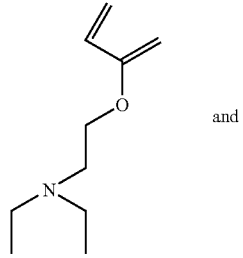 and 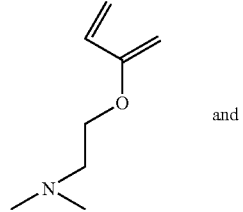 |
| | 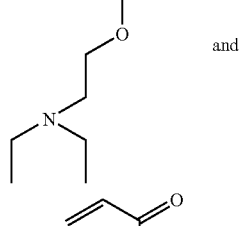 and  |

Example 4

Formulation and Fabric Treatment from Tertiary Amine-containing Polyacrylics of the Invention An aqueous solution of the tertiary amine poly(methacrylate) from Example 2 (11.6% w/w), acetic acid (6.0% w/w) and $MgCl_2$ (1.5%, w/w) was prepared.

Cotton fabric samples (15×13 inch square) were dipped in the above finish solution. After padding under pressure at 30 psi, the fabric swatches were cured at 150° C. for 1 minute.

Example 5

Formulation and Fabric Treatment from Prior Art Resin System

An aqueous solution of triethanol amine (4%), DMDHEU resin (20%) and $MgCl_2$ (4%, w/w) was prepared.

Cotton fabric samples (15×13 inch square) were dipped in the above solution. After padding under pressure at 30 psi, the fabric swatches were cured at 150° C. for 1 minute.

Example 6

Formulation and Treatment from Prior Art Alkanol Amines

A 100.0 g aqueous solution was prepared by adding 11.3% of polyethyleneimine (PEI) into 50 g of water and adjusting the pH to 4.0 with hydrochloric acid, followed by addition of 0.1% WetAid NRW (Noveon). 2.9 Grams of alkylated DMD-HEU (Sedgere PCR-2) and additional water were added to make up 100.0 g.

Cotton fabric samples (15×13 inch square) were dipped in the above solution. After padding under pressure at 30 psi, the fabric swatches were cured at 150° C. for 1 minute.

Example 7

Performance Testing on Fabrics

Standard home launderings (HL) were done based on AATCC method 124-2001, but using 28 grams of granular detergent with bleach instead of using 66 grams of 1993 AATCC standard reference detergent.

a. Odor Absorption

Butyric acid is one of the byproducts after sweat is decomposed by bacteria. It is responsible for body odor, so it was chosen to simulate body odor in sniff testing. During testing, different concentrations of butyric acid were dropped onto fabric samples. The smell panel sniffed the spot on the fabric from 1 inch away using a paper guide. The concentration of butyric acid that could be detected by the panel member was considered to be the butyric acid absorption level of the fabric. Dropping and smelling were continued until all people can smell butyric acid on the fabric. The average of the smell test results for each sample was determined.

The treated fabrics from Example 4 of the present invention and from Examples 5 and 6, having prior art finishes, were tested for odor absorption according to the above. The results are shown below in Table B. It shows that all of the treated fabrics can absorb organic acid malodor at least for 30 home laundries. The chemical finishing is durable.

TABLE B

|  | 1 HL | 30 HL |
|---|---|---|
| Untreated (ppm) | 500 | 500 |
| Example 4 (ppm) | 2500 | 2500 |
| Example 5 (ppm) | 2000 | 2000 |
| Example 6 (ppm) | 2000 | 2000 | b. Physical Strength

Tearing strength ("Elmendorf tear") is measured by ASTM test method D 1424-96 after one home laundry and tumble dry. Tensile strength is according to ASTM test method D5304-95 after one home laundry and tumble dry.

The tearing strength and tensile for fabrics finished according to Example 4 and Example 5 were compared in Table C. It is clear that the tear strength and tensile strength were damaged dramatically when the fabrics were finished with the resin system of Example 5. However, physical strength loss, including both tear and tensile strengths, has been substantially improved by finishing with tertiary amine-containing polyacrylics of the invention.

TABLE C

|  | Tensile Strength | | Tear Strength | |
|---|---|---|---|---|
|  | Warp (N) | Fill (N) | Warp (N) | Fill (N) |
| Untreated | 754.9 | 285.3 | 13.7 | 7.0 |
| Example 4 | 594.3 | 241.4 | 13.0 | 6.0 |
| Example 5 | 244.5 | 67.7 | 7.1 | 3.3 | c. Yellowing

Whiteness index of untreated fabrics and treated fabrics was measured by Datacolor 600 spectrum following AATCC Test Method 110-2000.

The whiteness index for fabrics treated according to Example 4 and Example 6 were compared with untreated fabrics right after treatment and after 30 home laundries, as shown in Table D. Whiteness index for fabrics treated with PEI (Example 6) dropped 40% right after treatment. After continuous 30 home laundries, the whiteness index decreased almost 60%. In contrast, the whiteness index for fabrics treated with the tertiary amine-containing polymers of the invention (Example 4) only dropped 13% after treatment, and it remained almost the same after 30 HLs. This whiteness index difference could be fixed by fluorescent whitening agent (FWA) easily.

TABLE D

|  | 0 HL | 30 HL |
|---|---|---|
| Untreated | 105 | 93 |
| Example 6 | 62 | 41 |
| Example 4 | 91 | 89 |

Example 8

Synthesis of Ether-Containing Poly(Tertiary Amine)

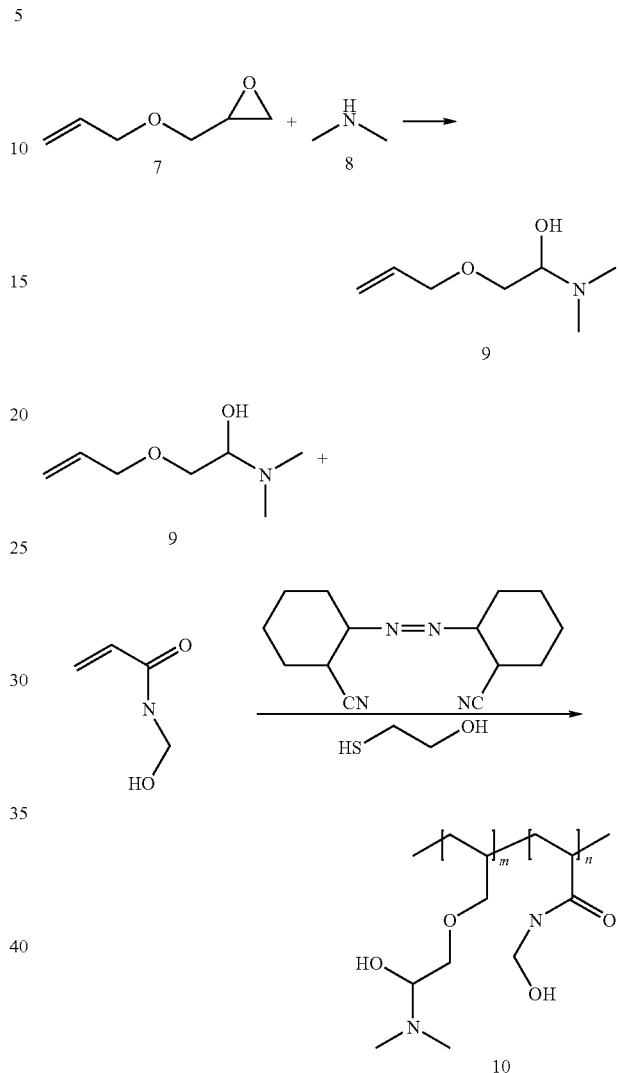

Allyl glycidyl ether (7) and dimethyl amine (8) are charged into a flask with methylene chloride. The solution is stirred for 2 hours. The suspension is refluxed and filtered. Product (9) is obtained after the solvent is removed by distillation. N-(hydroxymethyl)acrylamide (4), amine-containing allyl glycidy ether (9) and the initiator 1,1'-azobis(cyclohexanecarbonitrile) (Vazo® 88, Dupont) are then charged in the flask. The solution is stirred overnight at 80° C. under nitrogen. The copolymer (10) of tertiary amine-containing allyl glydidyl ether and N-(hydroxylmethyl)acrylamide is obtained.

We claim:

1. A finish for a cellulosic fibrous substrate, the finish comprising:
   i) a suitable crosslinker;
   ii) a volatile solvent; and
   iii) a tertiary amine-containing polymer of formula (I):

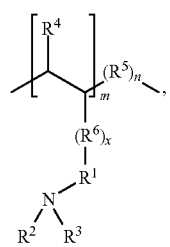

wherein:
R¹ is independently based on an alkyl group, a hydroxyalkyl group or a tertiary amine-containing alkyl group;
each of R² and R³ is independently an alkyl group, a hydroxyalkyl group or a tertiary amine-containing alkyl group;
R⁴ is hydrogen or an alkyl group;
R⁵ is N-(hydroxymethyl)acrylamide;
R⁶ is an ester group, an ether group, an amide group or a tertiary amine-containing group;
each of m and n is a positive integer of about 10 to about 1,000,000; and
x is zero or 1.

2. A finish according to claim 1 wherein R¹ is based on an alkyl group.
3. A finish according to claim 1 wherein x is one.
4. A finish according to claim 3 wherein R⁶ is an ester group.
5. A finish according to claim 1 wherein the ratio of m to n is from about 1:100 to about 100:1.
6. A finish according to claim 1 wherein the ratio of m to n is from about 1:10 to about 10:1.
7. A finish according to claim 1 wherein the ratio of m to n is about 6:1.
8. A finish according to claim 1 further including a catalyst.
9. A finish for a cellulosic fibrous substrate, the finish comprising:
  i) a suitable crosslinker;
  ii) a volatile solvent;
  iii) a first tertiary amine-containing polymer comprising a poly[N,N-(dimethylaminoethyl)aminoethyl methacrylate]; and
  iv) a second tertiary amine-containing polymer comprising one or more of:
    a. an acrylic polymer of formula (5):

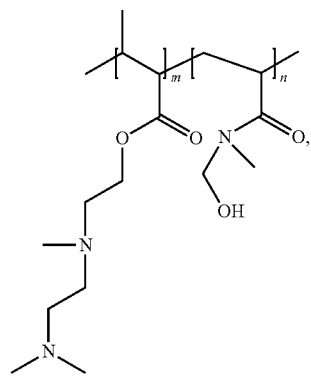

wherein the ratio of m to n is from about 1:100 to about 100:1;

b. an acrylic polymer that is the reaction product of any one of:
  1. monomers of formulas:

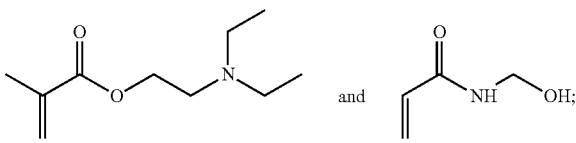

2. monomers of formulas:

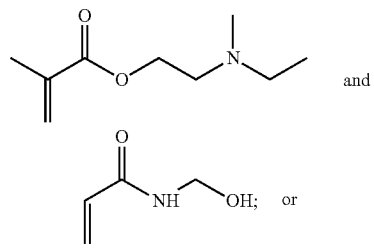

3. monomers of formulas:

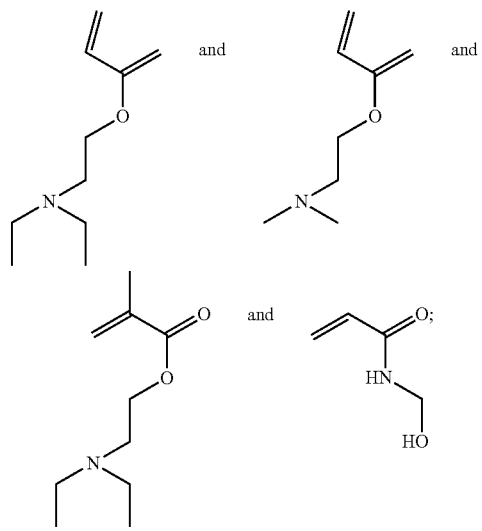

c. an acrylic polymer of formula (10):

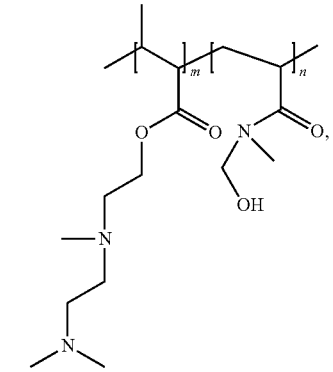

wherein the ratio of m to n is from about 1:100 to about 100:1;
d. a poly[N,N-(diethylamino)ethyl methacrylate]; or
e. a poly[N,N-(diethylamino)methyl methacrylate].

10. A finish according to claim 9 wherein the second tertiary amine-containing polymer comprises a homopolymer, a copolymer, or a terpolymer.

11. A finish according to claim 9 wherein the ratio of m to n is from about 1:10 to about 10:1.

12. A finish according to claim 9 further including a catalyst.

13. A finish for a cellulosic fibrous substrate, the finish comprising:
i) a suitable crosslinker;
ii) a volatile solvent; and
iii) a tertiary amine-containing polymer of formula (I):

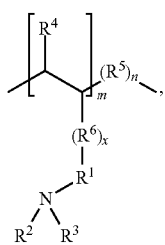
(I)

wherein:
R$^1$ is independently based on an alkyl group, a hydroxyalkyl group or a tertiary amine-containing alkyl group;
each of R$^2$ and R$^3$ is independently an alkyl group, a hydroxyalkyl group or a tertiary amine-containing alkyl group;
R$^4$ is hydrogen or an alkyl group;
R$^5$ includes a hydroxyl-reactive functional group;
R$^6$ is an ester group, an ether group, an amide group or a tertiary amine-containing group;
each of m and n is a positive integer of about 10 to about 1,000,000; and
x is zero.

14. A finish according to claim 13 wherein R$^1$ is based on an alkyl group.

15. A finish according to claim 13 further including a catalyst.

16. A finish for a cellulosic fibrous substrate, the finish comprising:
i) a suitable crosslinker;
ii) a volatile solvent; and
iii) a tertiary amine-containing polymer of formula (I):

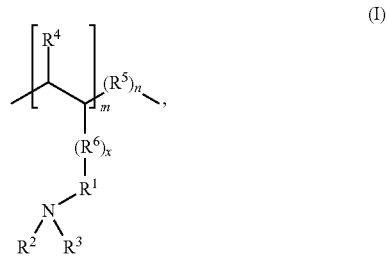
(I)

wherein:
R$^1$ is independently based on an alkyl group, a hydroxyalkyl group or a tertiary amine-containing alkyl group;
each of R$^2$ and R$^3$ is independently an alkyl group, a hydroxyalkyl group or a tertiary amine-containing alkyl group;
R$^4$ is hydrogen or an alkyl group;
R$^5$ includes a hydroxyl-reactive functional group;
R$^6$ is an ether group;
each of m and n is a positive integer of about 10 to about 1,000,000; and
x is zero or 1.

17. A finish according to claim 16 wherein R$^1$ is based on an alkyl group.

18. A finish according to claim 16 wherein x is one.

19. A finish according to claim 16 wherein the ratio of m to n is from about 1:100 to about 100:1.

20. A finish according to claim 16 wherein the ratio of m to n is from about 1:10 to about 10:1.

21. A finish according to claim 16 wherein the ratio of m to n is about 6:1.

* * * * *